(12) United States Patent
Dimmit et al.

(10) Patent No.: US 6,274,068 B1
(45) Date of Patent: Aug. 14, 2001

(54) SYNTHESIS OF 2-HYDROXYARYLALDEHYDES

(75) Inventors: Jeffrey Howard Dimmit, Gilbert, AZ (US); Mark Alan Kearns, Joplin, MO (US); William H. Chambless, Plano, TX (US)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 0 days.

(21) Appl. No.: 09/209,518

(22) Filed: Dec. 10, 1998

Related U.S. Application Data

(63) Continuation of application No. 08/861,135, filed on May 21, 1997, now Pat. No. 5,856,583.

(51) Int. Cl.$^7$ ................................ C07F 3/02; C07C 45/00
(52) U.S. Cl. ...................... 260/665 G; 568/437; 568/426
(58) Field of Search ................................ 568/433, 432, 568/426, 437; 260/665 G

(56) References Cited

U.S. PATENT DOCUMENTS

| | | | |
|---|---|---|---|
| 5,354,920 | * 10/1994 | Cox et al. | 568/437 |
| 5,763,675 | 6/1998 | Levin | 568/433 |

OTHER PUBLICATIONS

Robert Aldred, et al.: "Magnesium–mediated ortho–Specific Formylation and Formaldoximation of Phenols", Journal of the Chemical Society, Perkin Transactions 1, Jul. 7, 1994, pp. 1823–1831, XP002110000.

* cited by examiner

*Primary Examiner*—Sreeni Padmanabhan
(74) *Attorney, Agent, or Firm*—John E. Drach

(57) ABSTRACT

A method for the preparation of 2-hydroxyarylaldehydes from an aryloxy magnesium compound and formaldehyde, which comprises reacting at a temperature from 40–120° C., an aryloxy magnesium compound having an aryloxy anion and a non-aryloxy anion and in which (a) the non-aryloxy anion is more basic than the aryloxy anion such that when the aryloxy magnesium compound is brought into contact with an acidic species, the acid reacts more preferentially with the non-aryloxy anion to form an aryloxy magnesium salt and (b) the aryloxy anion has at least one free position ortho to the hydroxyl group in the aryloxy anion, with formaldehyde or a compound capable of giving rise to formaldehyde under the reaction conditions in the presence of a polar co-solvent capable of providing the non-aryloxy anion in the aryloxy magnesium compound characterized in that the non-aryloxy anion is selected from the group consisting of an oxide, a hydroxide, a carboxylate, a sulphate and a nitrate.

8 Claims, No Drawings

SYNTHESIS OF 2-HYDROXYARYLALDEHYDES

This application is a continuation of U.S. application Ser. No. 08/861,135 filed May 21, 1997 now U.S. Pat. No. 5,856,583.

TECHNICAL FIELD OF THE INVENTION

This invention relates to a process for making 2-hydroxyarylaldehydes by reacting an aryloxy magnesium compound with formaldehyde or a compound capable of generating formaldehyde in situ under certain reaction conditions.

BACKGROUND OF THE INVENTION

Ortho-formylated phenols and their derivatives are valuable intermediates in the chemical, pharmaceutical and mining industries. Therefore, processes for making hydroxyarylaldehydes, and in particular, 2-hydroxyarylaldehydes, have been well researched. It is well recognized that such hydroxyarylaldehydes can be made by reacting magnesium phenoxides with formaldehyde.

For instance, Casiraghi et al. described in J. C. S. Perkin I (1978) pp. 318 et seq. that aryloxymagnesium bromide alone or its complexes with hexamethylphosporamide (HMPA) can be reacted with formaldehyde in refluxing benzene and conclude that the absence of HMPA leads to the formation of dihydroxydiphenylmethanes whilst the formation of the desired 2-hydroxyarylaldehydes is promoted only by the presence of stoichiometric amounts of the HMPA ligand. This latter reaction is said to occur via an oxidation-reduction process, promoted by HMPA, between an intermediate 2-hydroxybenzyl alcohol intermediate and formaldehyde. The difference in acidity between the free and HMPA-complexed magnesium counterion is invoked to explain the two reaction pathways.

Similarly, Aldred et al. describe in J. C. S. Perkin I (1994) at pp. 1823 et seq. the deprotonation of phenols using magnesium methoxide, followed by distillative removal of free methanol and addition of paraformaldehyde to generate, by an ortho-specific magnesium-mediated formulation, the corresponding salicylaldehyde magnesium salts from which the salicylaldehydes are isolated by acidic work-up. They further disclose that addition of aqueous hydroxylamine sulphate to the salicylaldehyde magnesium salts, in place of the acid work-up, yields the corresponding salicylaldoximes.

Similar methods are also described in: U.S. Pat. No. 5,260,487 in which 2-hydroxyarylaldehyde is made by reacting a magnesium bis-hydrocarbyloxide, derived at least in part from a hydroxyaromatic compound having at least one free ortho position to the hydroxyl group with formaldehyde under substantially anhydrous conditions; and U.S. Pat. No. 5,354,920 in which 2-hydroxyarylaldehyde is made by reacting an aryloxymagnesium halide with formaldehyde under substantially anhydrous conditions in the presence of a polar organic solvent other than HMPA or 1,3-dimethyl-3,4,5,6-2(1H)-pyrimidone.

It has now been found and the present invention relates to a process in which 2-hydroxyarylaldehydes are made with an active species that contains only non-hydrocarbyloxy ligands attached to the magnesium aryloxide moiety.

SUMMARY OF THE INVENTION

The present invention comprises a process for the preparation of 2-hydroxyarylaldehydes from an aryloxy magnesium salt and formaldehyde, the process comprising reacting at a temperature from 40–120° C.

I. an aryloxy magnesium compound, having an aryloxy anion and a non-aryloxy anion and in which (a) the non-aryloxy anion is more basic than the aryloxy anion such that when the aryloxy magnesium compound is brought into contact with an acidic species, the acid reacts more preferentially with the non-aryloxy anion to form the desired aryloxy magnesium salt and (b) the aryloxy anion has at least one free position ortho to the hydroxyl group in the aryloxy anion, with II. formaldehyde or a compound capable of giving rise to formaldehyde under the reaction conditions, in the presence of a polar co-solvent capable of providing the non-aryloxy anion in the aryloxy magnesium compound characterized in that the non-aryloxy anion is selected from the group consisting of an oxide, a hydroxide, a carboxylate, a sulphate an a nitrate.

The present invention relates to the creation of 2-hydroxyarylaldehydes. The present invention provides a process for making 2-hydroxyarylaldehydes by reacting an aryloxy magnesium compound with formaldehyde or a compound capable of generating formaldehyde in situ at a temperature from 40–120° C. by a process in which the active species that contains only non-hydrocarbyloxy ligands attached to the magnesium aryloxide moiety.

The present invention also has the ability to tolerate the presence of water.

Finally, the present invention allows the use of water as the acidic species in order to generate non-aryloxy anions in salt as eg. oxide or hydroxide.

DETAILED DESCRIPTION OF THE INVENTION

The aryloxy magnesium salt is suitable derived from an aryloxy magnesium compound which in turn is derived by reacting a phenolic compound which has at least one of the ortho positions, i.e. the 2- and/or 6-positions of the aromatic ring with respect to the carbon carrying the phenolic hydroxyl group, free. The meta and para positions in the aromatic nucleus may carry substituents which are inert under the reaction conditions. Suitable examples of such substituents include one or more of hydrogen atoms; halogen atoms; alkyl, cycloalkyl, and alicyclic groups, aryl groups, alkaryl groups, aralkyl groups having 1–36 carbon atoms; alkoxy groups, aryloxy groups which have from 1–30 carbon atoms; acyl groups which have from 1–24 carbon atoms; and any combinations thereof.

They aryloxy magnesium compound can be prepared by any of the methods known to those skilled in the art. For instance, magnesium in the form of its alkoxide, e.g. methoxide can be reacted with a reactant capable of providing the aryloxy group, i.e. a phenolic compound, such as e.g. paranonyl phenol, in the presence of a non-polar solvent, such as e.g. benzene, toluene, xylene or cyclohexane, optionally in the presence of a polar co-solvent. Examples of polar co-solvents that may be used include one or more of: lower C1–C4 alcohols such as, e.g., methanol and ethanol; amines such as e.g. triethylamine or pyridine; amides such as, e.g., dimethylformamide and N,N-dimethylacetamide; sulphoxides such as e.g., dimethyl sulphoxide; mono-glyme, di-glyme and tri-glyme; and ethers such as e.g., diethyl ether, diphenyl ether and tetrahydrofuran.

The reaction mixture is heated to reflux to allow the magnesium to dissolve. The phenolic compound, e.g. nonyl phenol, is then added to this solution of magnesium alkoxide in a non-polar solvent with agitation to ensure good mixing of the reactants. The mixture is suitably heated for a period to facilitate complete of the reaction. The temperature for this step is preferably within the range from 25° C. to the boiling point of the reaction mixture. The reaction is preferably run at or near the boiling point of the solvent used for the reaction. For example, if toluene is used as the solvent and magnesium methoxide is the alkoxide, the reaction mixture is preferably run at a temperature of about 65° C. The duration of the reaction is generally in the range from 30 minutes to several hours depending upon the reaction temperature employed. In general, lower temperatures will require longer reaction times to complete the conversion. When the reaction is run at or near the boiling point of the solvent system used, a reaction time of 30 to 60 minutes should be sufficient for completion of the conversion. The relative mole ratios of the phenolic compound to the magnesium alkoxide is suitable in the range from about 0.9:1 to about 1.1:1, and is preferably about 1:1. Subsequently, the non-polar solvent and the polar co-solvent are then removed as an azeotrope from the reaction mixture by fractional distillation. The reaction may be carried out at ambient or under reduced pressure, the latter being used to facilitate the removal of volatile by-products of the reaction. The resultant aryloxy magnesium compound is then reacted with a compound capable of providing the desired non-aryloxy anion such as e.g. an oxide, a hydroxide, a carboxylate, sulphate or a nitrate anion to form the desired aryloxy magnesium salt. An example of a compound capable of providing a carboxylate anion s glacial acetic, which provides an acetate anion. The relative mole ratios of the aryloxy magnesium compound to the compound capable of giving rise to the non-aryloxy anion is suitably in the range from about 0.9:1 to about 1.1:1, and is preferably about 1:1. The addition of the compound capable of giving rise to the non-aryloxy anion is suitably carried out over a short duration e.g. from 1 to 3 hours at a temperature in the range from about 60–80° C. and at either ambient or reduced pressure, e.g. about 350 mm Hg.

When the addition of the compound providing the non-aryloxy anion is complete, the desired aryloxy magnesium salt is generated and is ready for the next stage of the reaction. In this context, it should be understood that due to the greater affinity of the non-aryloxy anions towards the aryloxy magnesium cation when compared with the alkoxy ligands of prior art, the final aryloxy magnesium salt so formed is substantially free of any aryloxymagnesium alkoxide.

The addition of the formaldehyde reactant to the aryloxy magnesium salt can then be commenced. The relative mole ratios of the aryloxy magnesium salt to the (para) formaldehyde for this state of the reaction is suitable in the range from about 2 to 3.5, preferably from about 2.5 to 3. This stage of the reaction is carried out at a temperature in the range suitable from 40–120° C., and preferably from 45–100° C. The formaldehyde may be added as a gas, a solid or as a solution of solid paraformaldehyde in an anhydrous solvent over a duration, e.g., of 1 to 10 hours and during this addition the reaction temperature is suitably in the range of 60–90° C. Whichever form is used, the reaction mixture and the added reactants, with the exception of paraformaldehyde, are substantially anhydrous. During this step of addition of formaldehyde, any volatile reaction by-products formed are removed continually from the reaction mixture by distillation.

When the addition of formaldehyde is completed, the reaction temperature is suitably raised to about 70–100° C. and maintained at that temperature for a further duration, e.g., 2–5 hours, preferably about 3 hours. Thereafter, a strong acid solution, such as e.g. a 10% aqueous solution of sulphuric acid, is added to the reaction mixture and stirred for a duration, e.g., 1 hour and the reaction mixture is then allowed to undergo phase separation. Upon separation of the phases, the organic phase is washed several times with water, the organic phase dried and rendered free of any solvents. The residual product is crude 2-aryloxyaldehyde. Where para-nonyl phenol is used, the crude product will be 5-nonylsalicylaldehyde. The crude product can be purified by methods known to those skilled in the art such as, e.g., distillation under reduced pressure, especially if the product aldehyde is of a relatively higher molecular weight.

The aryloxyaldehydes so formed are very useful compounds. They can, for instance, be converted to the corresponding oximes and used as metal extractants. It can also be used in the pharmaceutical industry, in the production of perfumes and agrochemicals.

A feature of the present invention is its ability to tolerate the presence of water. For instance, commercial paraformaldehyde solid usually contains up to 7% by weight of water and this can readily be used in the present process. Moreover, the present process allows the use of water as the acidic species in order to generate non-aryloxy anions in the salt as e.g. oxide or hydroxide. This is a significant point of distinction over prior are processes such as those described in U.S. Pat. Nos. 5,345,920 and 5,260,487 both of which require the use of substantially anhydrous conditions.

The present invention is further illustrated when taken with reference to the following examples:

EXAMPLE 1

A 2-liter round-bottomed flask was charged with magnesium (12 g, 0.49 mol), methanol (285 ml), toluene (120 ml) and magnesium methoxide (10 ml solution of 7.4% by weight magnesium methoxide in methanol). The reaction mixture was heated to reflux and the magnesium dissolved. Para-nonyl phenol (112.4 g) was added in one portion to the reaction mixture. The flask was then rigged for a fractional vacuum distillation and an azeotrope of methanol/toluene was distilled off an internal temperature of 70° C. at a pressure of 350 mm Hg. Glacial acetic acid (28.5 ml, 0.5 mole) was added to the reaction mixture over a 1-hour period while maintaining the reaction temperature at 70° C. and the pressure at 350 mm Hg. When the addition of glacial acetic acid was complete, solid paraformaldehyde (46 g, a commercial sample containing 5–7% by weight water) was added over a 105-minute period. The reaction mixture was maintained at a temperature of 65° C. and a pressure of 350 mm Hg, during the addition of paraformaldehyde, and the volatile reaction by-products were continually removed. When the paraformaldehyde addition was complete, the reaction temperature was increased to 75° C. and maintained at that temperature for an additional 3 hours. Sulphuric acid (300 ml, 10% w/w) was added to the reaction mixture, which was then stirred for 1 hour. After phase separation, the organic phase was washed twice with 200 portion of water. The washed organic phase was then separated, dried and rendered free of the solvent to yield crude 5-nonyl salicylaldehyde. A 67% yield was obtained.

EXAMPLE 2

A 2 -liter round-bottomed flask was charged with magnesium (12 g, 0.49 mol), methanol (285 ml), toluene (120 mol) and magnesium methoxide (10 ml solution of 7.4% by weight magnesium methoxide in methanol). The reaction mixture was heated to reflux and the magnesium dissolved. Para-nonyl phenol (112.4 g) was added in one portion to the reaction mixture. The flask was then rigged for a fractional vacuum distillation and an azeotrope of methanol/toluene was distilled off to an internal temperature of 70° C. at a pressure of 350 mm Hg. Glacial acetic acid (28.5 ml, 0.5 mole) was added to the reaction mixture over a 1 hour period while maintaining the reaction temperatures at 70° C. and the pressure at 350 mm Hg. When the addition of glacial acetic acid was complete, pyridine (79 ml) and toluene (250 ml) were added. An azeotrope of methanol and toluene was distilled at pot temperature of 100° C. The reaction mixture was then cooled to 95° C. and solid paraformaldehyde (46 g, a commercial sample containing 5–7% by weight water) was added over a 45 minute period. The reaction mixture was maintained at a temperature of 95–100° C. during the addition of paraformaldehyde and volatile reaction by-products were continually removed by distillation. When the paraformaldehyde addition was complete, the reaction temperature was maintained at 95–100° C. for an additional 2 hours. Sulphuric acid (300 ml, 10% w/w) was added to the reaction mixture, which was then stirred for 1 hour. After phase separation, the organic phase was washed twice and 200 ml portions of water. The washed organic phase was then separated, dried and rendered free of the solvent to yield crude 5-nonyl salicylaldehyde. A 78% yield was obtained.

EXAMPLE 3

A 2-liter round-bottomed flask was charged with magnesium (24 g, 0.98 mol), methanol (570 ml), toluene (240 ml) and magnesium methoxide (10 ml solution of 7.4% by weight magnesium methoxide in methanol). The reaction mixture was heated to reflux and the magnesium dissolved. Para-nonyl phenol (224 g) was added in one portion to the reaction mixture. The flask was then rigged for a fractional vacuum distillation and an azeotrope of methanol/toluene was distilled off to an internal temperature of 70° C. at a pressure of 350 mm Hg. The mixture was cooled to 25° C. and toluene (300 ml) was added. Anhydrous hydrochloric acid (38 g) was added to the reaction mixture over a period of 1.5 hours. Methanol (200 ml) was then added to the mixture and the pot was rigged for an atmospheric pressure fractional distillation. An azeotrope of methanol/toluene was distilled off to a pot temperature of 100° C. The pot was then cooled to 90° C. and paraformaldehyde (94.8 g, a commercial sample containing 5–7% by weight water) slurried in toluene (200 ml) was added over a 1 hour period. During the addition of paraformaldehyde, volatile reaction by-products were continually removed. The reaction mixture was maintained at a temperature of 90° C. for an additional hour after the paraformaldehyde addition was complete. The reaction temperature was then cooled to 70° C. and sulphuric acid (300 ml, 10% w/w) was added to the reaction mixture, which was then stirred for 30 minutes. After phase separation, the organic phase was washed twice with 200 ml portion of water. The washed organic phase was then separated, dried and rendered free of the solvent to yield crude 5-nonyl salicylaldehyde. A 62% yield was obtained.

EXAMPLE 4

A 2-liter round-bottomed flask was charged with magnesium turnings (12.2 g, 0.50 mole), methanol (133 ml), toluene (60 ml), and magnesium methoxide solution (10 ml of an 8% w/w solution of magnesium methoxide in methanol). The reaction mixture was heated to 45° C. at which point the magnesium dissolution became vigorous. The temperature of the reaction mixture was maintained between 45 and 55° C. Para-dodecyl phenol (128.0 g, 0.50 mol) dissolved in toluene (125 ml) was added in one portion to the reaction mixture which was then maintained at 65° C. for one hour. Glacial acetic acid (30.1 g, 0.50 mol) was added over a 1 hour period, while maintaining the reaction mixture at reflux (65–66° C.). The reaction flask was then rigged for fractional distillation and the methanol/toluene azeotrope was distilled off until an internal temperature of 85° C. was reached. A total of 117 g of distillate, assaying 65% methanol and 35% toluene, was collected. Toluene (130 g) was added to the reaction mixture in one portion. Paraformaldehyde (45.0 g) slurried in toluene (90 g) was then added over a 90 minute period. During the addition, the reaction mixture was maintained at a temperature of 85–90° C. allowing a continuous distillation of the volatile reaction by-products. When the paraformaldehyde addition was complete, the reaction mixture was maintained at 90° C. for an additional 90 minutes. The reaction mass as then cooled to 35° C. and 500 ml of 20% v/v sulfuric acid was added. The hydrolysis mass was then stirred for an additional 45 minutes. After phase separation, the organic phase was washed twice with 200 ml portions of water. The washed organic phase was then separated, dried and rendered free of the solvent to yield crude 5-dodecyl salicylaldehyde. A 65% yield was obtained.

Although the invention has been described in detail, it is to be clearly understood that the same is by way of illustration and example only and is not to be taken by way of limitation, the spirit and scope of the invention being limited only to the terms of the appended claims.

We claim:

1. A phenoxy magnesium salt having an aryloxy anion and a non-aryloxy anion wherein the aryloxy anion at least one of the 2- and 6-positions of the aromatic ring is unsubstituted and wherein the meta and para positions carry hydrogen atoms; halogen atoms; alkyl and alicyclic groups, aryl groups, alkaryl groups, aralkyl groups having 1–36 carbon atoms; alkoxy groups, aryloxy groups which have from 1–30 carbon atoms; acyl groups which have from 1–24 carbon atoms; and any combinations thereof and wherein the non-aryloxy anion is selected from the group consisting of an oxide, a hydroxide, a carboxylate, a sulphate, and a nitrate.

2. The phenoxy magnesium salt of claim 1 having a dodecyl group at the para position.

3. The phenoxy magnesium slat of claim 1 having a nonyl group at the para position.

4. An aryloxymagnesium salt made by the process which comprises the steps of: (1) heating a reaction mixture comprising magnesium and an alcohol to reflux to allow the magnesium to dissolve by forming magnesium alkoxide and then adding a phenolic compound to the solution of magnesium alkoxide in a non-polar solvent with agitation to ensure good mixing of the reactants; (2) reacting the product of step (1) with a compound capable of providing a non-aryloxy anion selected from the group consisting of an oxide, a hydroxide, a carboxylate, a sulphate, and, a nitrate.

5. The compound of claim 4 wherein the aryloxy magnesium compound is derived by reacting a phenolic compound which has at least one of the ortho positions of the aromatic ring with respect to the carbon carrying the phenolic hydroxyl group, free.

6. The compound of claim 4 wherein the meta and para positions in the aromatic ring carry substituents which are inert under the reaction conditions.

7. The compound of claim 6 wherein the substituents in the meta and para positions in the aromatic ring are selected from the group consisting of hydrogen atoms; halogen atoms; alkyl and alicyclic groups; aryl groups, alkaryl groups and aralkyl groups having from 1–36 carbon atoms; alkoxy groups, aryloxy groups having from 1–30 carbon atoms; acyl groups having from 1–24 carbon atoms; and any combinations thereof.

8. The compound of claim 4 wherein the compound capable of providing a non-aryloxy anion is acetic acid.

* * * * *